United States Patent [19]

Marcus

[11] Patent Number: 5,212,099

[45] Date of Patent: May 18, 1993

[54] METHOD AND APPARATUS FOR OPTICALLY MEASURING CONCENTRATION OF AN ANALYTE

[75] Inventor: Michael A. Marcus, Honeoye Falls, N.Y.

[73] Assignee: Eastman Kodak Company, Rochester, N.Y.

[21] Appl. No.: 643,403

[22] Filed: Jan. 18, 1991

[51] Int. Cl.$^5$ .................................................. G01N 21/63
[52] U.S. Cl. ..................... 436/172; 436/164; 422/82.05; 422/82.06; 422/82.09; 422/82.11; 250/458.1; 250/459.1; 356/301; 356/312; 356/317
[58] Field of Search ................ 436/39, 147, 149, 164, 436/172, 805; 422/82.05, 82.06, 82.07, 82.08, 82.09, 82.11; 356/36, 38, 301, 312, 316, 317, 440, 445; 250/458.1, 459.1

[56] References Cited

U.S. PATENT DOCUMENTS

| | | | |
|---|---|---|---|
| 2,460,071 | 2/1945 | Davis | 252/408 |
| 2,505,079 | 9/1946 | Allen | 252/317 |
| 2,526,938 | 9/1946 | Davis | 252/408 |
| 2,580,737 | 1/1952 | Davis | 252/408 |
| 3,528,278 | 9/1970 | Sterling | 73/17 |
| 3,881,992 | 5/1975 | Ralston | 195/103.5 R |
| 3,926,052 | 12/1975 | Bechtel | 73/336 |
| 4,166,891 | 9/1979 | Elliott | 525/329 |
| 4,179,397 | 12/1979 | Rohowetz | 252/408 |
| 4,200,110 | 4/1980 | Peterson | 128/634 |
| 4,269,516 | 5/1981 | Lubbers et al. | 356/427 |
| 4,433,238 | 2/1984 | Adolfeson | 250/227 |
| 4,513,087 | 4/1985 | Giuliani | 436/96 |
| 4,517,456 | 5/1985 | Halsall et al. | 250/226 |
| 4,523,092 | 6/1985 | Nelson | 250/227 |
| 4,560,248 | 12/1985 | Cramp et al. | 350/96.34 |
| 4,608,344 | 8/1986 | Carter et al. | 436/34 |
| 4,612,289 | 9/1986 | Furuta et al. | 436/34 |
| 4,637,729 | 1/1987 | Schoch | 356/410 |
| 4,641,524 | 2/1987 | Tarvin | 73/335 |
| 4,681,855 | 7/1987 | Huang | 436/39 |
| 4,682,895 | 7/1987 | Costello | 356/402 |
| 4,703,175 | 10/1987 | Salour | 250/227 |
| 4,749,856 | 6/1988 | Walker | 250/227 |
| 4,764,671 | 8/1988 | Park | 250/227 |
| 4,830,513 | 5/1989 | Grego | 374/131 |
| 4,834,496 | 5/1989 | Blyler | 350/96.29 |
| 4,834,497 | 5/1989 | Angel | 350/96.29 |
| 4,841,778 | 6/1989 | Butler | 73/800 |
| 4,846,548 | 7/1989 | Klainer | 350/96.29 |
| 4,894,532 | 1/1990 | Peterson | 250/227 |

FOREIGN PATENT DOCUMENTS

55885/86 10/1986 Australia .
0184600A1 6/1986 European Pat. Off. .
2018418A 10/1979 United Kingdom .

OTHER PUBLICATIONS

W. Rudolp Seitz, "Chemical Sensors Based on Fiber Optics", Analytical Chemistry, vol. 96, No. 1, Jan. 1984, pp. 16A, 18A, 20A, 24A, 33A, & 34A.

(List continued on next page.)

Primary Examiner—James C. Housel
Assistant Examiner—Jeffrey R. Snay
Attorney, Agent, or Firm—Charles E. Snee, III

[57] ABSTRACT

Apparatus and method in which a beam of radiant energy (16) is passed into a medium at a wavelength selected to cause a response of an analyte in the medium or of a sensor (10,14) exposed to the medium, the sensor comprising a reagent whose optical properties change in response to the presence of the analyte in the medium. A perturbing pulse of energy (22) is passed into the medium to alter the response of the analyte or reagent to the beam of radiation; and the time rates of change in the intensity of the transmitted radiant energy are measured (18,24,26,28) while the intensity is changing due to the perturbing pulse, after each such perturbing pulse starts or ends or both, such rates of change being proportional to the concentration of the analyte in the medium. Both the beam of radiant energy and the perturbing pulse may be passed through optic fibers into the medium or sensor.

56 Claims, 3 Drawing Sheets

OTHER PUBLICATIONS

A. P. Russell and K. S. Fletcher, "Optical Sensor for the Determination of Moisture", Analytica Chemica Acta, vol. 170, 1985, pp. 209–216.

Otto S. Wolfbeis, Bernard P. H. Schaffar and Erhard Kaschnitz, "Optical Fiber Titrations-Part3.-Construction and Performance of a Fluorometric Acid-Base Titrator with a Blue LED as a Light Source", Analyst pp. 1331–1334.

D. S. Ballantyne & H. Wohltjen, "Optical Waveguide Humidity Detector", *Analytical Chemistry*, vol. 58, 1986, pp. 2883–2885.

H. E. Posch and O. S. Wolfbeis, "Optical Sensors, 13: Fibre-Optic Humidity Sensor Based on Fluorescence Quenching", Sensors & Actuators, pp. 77–83.

B. Narayanaswamy & F. Sevilla III, "Optical fibre sensors for chemical species", *Journal Phys. E. Sci. Instrum.*, vol. 21, 1988, pp. 10–17.

Chu Zhu, F. V. Bright, W. A. Wyatt & G. M. Hieftje, "A New Fluorescence Sensor for Quantification of Atmospheric Humidity", Abstract from Program of Pittsburgh Conference on Analytical Chemistry and Applied Spectroscopy, 1987, p. 606.

R. Rueter, H. Franke, "Monitoring humidity by polyimide lightguides", Appl. Phys. Lett., vol. 52. No. 10, Mar 1988, pp. 778–779.

M. R. Shahriari, G. H. Sigel, Q. Zhou, "Porous Fiber Optic for a High Sensitivity Humidity Sensor", Rutgers Univ., Fiber Optics Mat. Res. Prog, Jan. 1988 p. 1.

K. Ogawa, S. Tsuchiya, "Humidity Sensing Effects of Optical Fibres with Microporous $SiO_2$ Cladding", *Electronics Letters*, V24N1, Jan. 1988, pp. 42–43.

S. Muto, A. Fukasaawa, M. Kamimura, F. Shinmura, H. Ito, "Fiber Humidity Sensor Using Fluorescent Dye-Doped Plastics", Japanese Journal of Appl. Physics vol. 28, No. 6, Jun. 1989, pp. L1065–L1066.

METHOD AND APPARATUS FOR OPTICALLY MEASURING CONCENTRATION OF AN ANALYTE

DESCRIPTION

1. Technical Field

This invention is related to methods and apparatus for measuring the concentrations of analytes in fluid mediums. More particularly, this invention concerns measuring such concentrations by monitoring changes in the effect the analyte has on radiant energy passed through the medium or through a sensor comprising a reagent exposed to the medium and correlating such changes to the concentration of the analyte.

2. Background Art

A variety of techniques have been developed for monitoring the concentration of an analyte in a fluid medium based on the effect the analyte has on the optical properties of the medium or based on the response of a sensor exposed to the analyte in the medium. For example, cobalt chloride has been used for decades in indicators of various types which rely on the change in color of the compound in response to changes in ambient humidity. Cobalt bromide, copper chloride, magnesium chloride, nickel chloride, cobalt thiocyanate, barium chloride, cobalt iodide and vanadium chloride, used alone or in various combinations, also have been demonstrated as humidity sensors whose color changes with changes in ambient humidity. Such sensing compounds have been used in combination with various carrier materials such as polymer matrices including sol gels, gelatin, polyvinylpyrrolidone, Nafion polymer and polymethylmethacrylate. Diethylaluminum hydride-2-isoquinoline complexes have also been used as humidity indicators. Rhodamine 6 G in a Nafion matrix also has been used as a humidity detector since its absorbance at a wavelength of 520 nm increases with increasing ambient humidity and its fluorescence at 572 nm also changes as a function of humidity. Umbelliferon dye in a matrix of polymethylmethacrylate also has been shown to be sensitive to humidity since its absorbance at 370 nm and fluorescence at 420 nm are functions of humidity in the ambient. Other sensors depend on quenching of fluorescence, such as those using perylenedibutrate and N-substituted derivatives of perylenetetracarboxylic acid bisimides in appropriate polymer matrices. Porous silicon oxide/titanium oxide and silicon oxide coatings have also been used as humidity sensors. Optic fibers clad with silicon oxide or plasma polymerized hexamethyldisiloxane and ammonia also have been shown to be sensitive to humidity. Various polyimide coatings are also sensitive to moisture in the ambient.

Reagents and other materials also are known whose optical properties change in response to analytes other than moisture. The following are representative of the many examples which can be found in the literature. Oxygen in the ambient can be sensed by perylene dibutyrate dye which, when excited at 450 nm, will produce a green fluorescence at 520 nm, which fluorescence is quenched by oxygen in the ambient. Oxygen can also be sensed by pyresine butryic acid whose fluorescence also is quenched by oxygen in the atmosphere. Oxygen can be detected by 9,10 diphenyl anthracene. Ammonia can be sensed by oxazine perchlorate dye which changes color reversibly in response to ammonia in the ambient. Bromocresol purple changes its absorbance at 580 nm due to the presence of ammonia, shifting from yellow to blue. Ammonia also can be detected by indophenol with casein fluorophase whose fluorescence changes in response to ammonia in the ambient. Glucose can be sensed with fluorescein labelled dextran and concanavillin A on Sepharose. Triphenyl methane dyes change absorbance in the presence of many organic solvents. Similarly, the absorbance of 3,3,diphenylphthalate crystal violet lactone changes in the presence of many organic solvents. Penicillin can be detected by the enzyme penicillinase on glutaraldehyde bound with fluorescein isothiocyanate, since the enzyme binds to penicillin and quenches its fluorescence. Sodium picrate becomes blue in the presence of hydrogen cyanide. Iodine changes from purple to clear in the presence of cyanide ions. Sulphate ions can be sensed using barium chloride which changes from clear to white opaque. Bile acid can be sensed using the reagent $3\alpha$-hydroxysteroid dehydrogenase together with co-enzyme NAD; since in the presence of the reagent, bile acid converts NAD to NADH which fluoresces at 480 nm upon excitation at 340 nm. Iron can be detected by 1,10 phenanthroline which becomes red as the concentration of iron increases. Aluminum can be detected by pyrocatechol which loses its violet color as the concentration of aluminum increases. Oxazine perchlorate is sensitive to the presence of hydrazine and pyredene. Halides can be detected by acridunium and quinollinium indicators whose fluorescence is quenched by their presence. Chlorine can be sensed by orthocolidine.

In all of the examples mentioned, the optical properties of the reagent material, such as its fluorescence, its absorbance, its tendency to scatter, its reflectance or some combination of these characteristics, are changed as the concentration changes in the ambient of a particular analyte such as water vapor. While a variety of sensors based on such reagents have been developed and some have received a certain amount of acceptance in industry, problems have continued to exist which have rendered such sensors unsuitable for many applications. The sensors tend to be rather slow to respond to changes in the concentration of the analyte, not infrequently requiring from many seconds to several minutes to stabilize when the concentration changes. This sort of response is not acceptable for many applications, particularly where small changes in concentration can have major effects on a manufacturing process. The sensors often are easily damaged by long exposure to saturated analyte environments, leading to a loss of the function of the sensitive reagent material, which makes recalibration necessary. In some instances, saturation of the sensor is essentially irreversible which eventually requires replacement of the sensor. If the sensor is incorporated into an optic fiber, breakage of the fiber in the sensitive area typically requires recalibration, as does loss of a significant portion of the reagent material from the sensitive area. The response of some sensors tends to drift slowly due to temperature drift and other environmental effects.

SUMMARY OF THE INVENTION

The primary objective of this invention is to provide an improved optical method and apparatus for measuring the concentration of an analyte in a fluid medium, which are rapidly responsive to changes in the concentration of the analyte.

Another objective of this invention is to provide such an apparatus and method which are capable of continued, accurate operation even after the sensor has been damaged by breakage or loss of some of its reagent material, without the need to recalibrate.

Still another objective of this invention is to provide such an apparatus and method in which saturation of the sensor is minimized.

Yet another objective of this invention is to provide such an apparatus and method in which drift of the sensor response is minimized.

These objectives are given only by way of illustrative examples; thus other desirable objectives and advantages inherently achieved by the disclosed invention may occur or become apparent to those skilled in the art. Nonetheless, the scope of the invention is to be limited only by the appended claims.

In accordance with one embodiment of the method and apparatus of the invention, a beam of ultraviolet, visible or infrared radiant energy is directed, preferably continuously, into a medium containing an analyte of interest, the radiation being at a wavelength and power level selected to cause a measurable response of the analyte. The analyte may respond by fluorescing, by absorbing a portion of the radiant energy, by scattering a portion of the radiant energy or by reflecting a portion of the radiant energy; and the response is detected. Periodically, a perturbing pulse of energy is directed into the medium to alter in a controlled manner the response of the analyte to the beam of radiant energy; and the response is detected while the response is changing due to said perturbing pulse, after each said perturbing pulse starts or ends or both. The perturbing pulse may be ultraviolet, visible or infrared radiant energy, acoustic energy, energy from an electrical or magnetic field, energy from a microwave generator or energy from a heat source, depending on the medium and the analyte under consideration. The time rate of change of the response is determined and is correlated to the concentration of the analyte. Preferably, the response is a change in the intensity of the radiation leaving the medium which can be correlated to concentration of the analyte by measuring the time rate of change of the intensity.

In accordance with another, preferred embodiment of the method and apparatus of the invention, a reagent is provided whose optical properties change in response to the concentrations of the analyte. The reagent may respond by fluorescing, by absorbing a portion of the radiant energy, by elastically or inelastically scattering a portion of the radiant energy or by reflecting a portion of the radiant energy. The reagent is exposed to the analyte in a medium and a beam of ultraviolet, visible or infrared radiant energy is directed into the reagent at a wavelength and power level selected to affect the beam of radiant energy as a function of the concentration of the analyte; and the effect of the reagent on the beam is detected. Periodically, a perturbing pulse of energy is directed into the reagent to alter in a controlled manner the optical spectral characteristics of the reagent as a function of analyte concentration; and the effect of the reagent on the beam is detected while the effect is changing due to said perturbing pulse, after each said perturbing pulse starts or ends or both. The perturbing pulse may be ultraviolet, visible or infrared radiant energy, acoustic energy, energy from an electrical or magnetic field, energy from a microwave generator or energy from a heat source, depending on the medium, the reagent and the analyte under consideration. As in the previously described embodiment, the response or effect of the reagent is a change in the intensity of radiation leaving the reagent which can be correlated to concentration by measuring the time rate of change of the intensity.

Preferably, the beam of radiation and the perturbing pulse are directed into the medium or reagent by one or more optic fibers. Where a reagent is used, it may be incorporated into a coating or cladding of the fiber at distributed locations along the length of the fiber or at the tip of the fiber which is immersed in the medium containing the analyte. The beam of radiation may be transmitted by the optic fiber directly through the medium or reagent or may be emitted from the fiber and focused on a sensor coated with the reagent, which reflects radiation back into the optic fiber in proportion to the concentration of the analyte. Planar optical waveguides also may be used to direct the beam of radiation to the medium or to the reagent, which may form a coating on the waveguide.

BRIEF DESCRIPTION OF THE DRAWINGS

The foregoing and other objectives, features and advantages of the invention will be apparent from the following more particular description of the preferred embodiments of the invention, as illustrated in the accompanying drawings.

DESCRIPTION OF THE PREFERRED EMBODIMENTS

Figure 1:
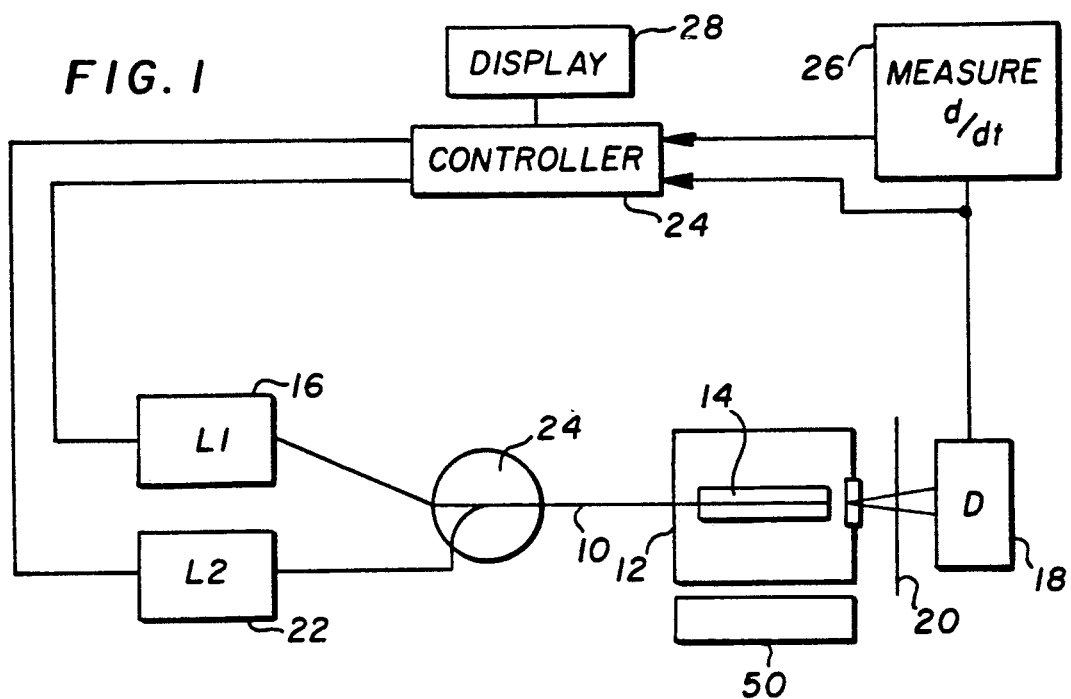
FIG. 1 illustrates schematically an optic fiber system for measuring the concentration of an analyte in a medium in accordance with the invention.

The following is a detailed description of the preferred embodiments of the invention, reference being made to the drawings in which the same reference numerals identify the same elements of structure in each of the several Figures.

In the embodiment of FIG. 1, an optic fiber 10 is extended into a plenum 12, such as a flow passage or zone for a fluid medium containing an analyte of interest. Within plenum 12, fiber 10 may be optically coupled to a cladding or coating 14 comprising a reagent whose optical properties change in response to changes in the concentration of the analyte in the fluid medium. In some applications, it may be desirable to surround fiber 10 within plenum 12 with a porous membrane, not illustrated, which allows only vapors of the analyte to reach cladding or coating 14 and helps to prevent overloading or saturating of the sensor. In either event, changes in the concentration of the analyte will cause corresponding changes in the intensity of radiant energy emitted from or reflected back along fiber 10 after being influenced by coating 14. A preferably continuous beam of ultraviolet, visible or infrared radiant energy is launched from a source 16 into fiber 10 at a wavelength and power level at which the sensitivity of the reagent in coating 14 is optimized for changes in the concentration of the analyte. The radiant energy may be emitted from fiber 10 and passed from plenum 12 to a suitable detectir 18 which measures the intensity of the radiant energy. Rather than emitting light from the end of fiber 10 to detector 18, it is also within the scope of the invention to reflect radiant energy back along the fiber to a detector, as will be discussed with regard to the embodiment of FIG. 5. In some applications, it may be desirable to include a filter 20 upstream of detector 18 for the purpose of shielding detector 18 from certain radiation, such as that provided by the pulsed source of radiant energy discussed in the following paragraph.

In accordance with the invention, a second, pulsed source of radiant energy 22 periodically launches perturbing pulses of radiant energy into fiber 10 by means of a conventional optical coupler 24. The perturbing pulses are at a wavelength and power level selected to alter in a controlled manner the optical spectral characteristics of the reagent in coating 14 as a function of analyte concentration, thereby changing the effect of the reagent on the radiant energy emitted from fiber 10 to detector 18. Thus, the change in the effect of the reagent is achieved by adding energy to the reagent which may cause a rise in the temperature of the reagent, a phase change of the reagent or a desorption of the analyte. The perturbing pulse may be the preferred ultraviolet, visible or infrared radiant energy; however, as also discussed with regard to the embodiment of FIG. 5, the desired change in the effect of the reagent also can be achieved by acoustic energy, energy from an electrical or magnetic field, energy from a microwave generator or energy from a heat source, depending on the particular application and the analyte under consideration. Whatever the source of the perturbing pulse, its function is to alter the amount of analyte present in the path of the beam of radiation from source 16 which will thus alter the optical transmission, fluorescence, scattering or reflectance due to the presence of the analyte.

In general, the amount of energy supplied to the system by the perturbing pulse is given by the absorption coefficient of the medium at the wavelength of the perturbing pulse. Let $P_i$ be the power in watts of the incident perturbing pulse; $P_a$, the power in watts of the absorbed perturbing pulse; and $P_t$, the power in watts of the transmitted perturbing pulse. The optical density OD of the medium can be expressed as follows:

$$OD = \log (P_i/P_t) = \epsilon c l$$

in which $\epsilon$ is the molar absorption coefficient of the absorbing material in liters per mole-cm, c is the concentration of the absorbing material and l is the effective length over which absorption takes place. The amount of energy absorbed by the sensing medium can be expressed as follows:

$$P_a = P_i - P_t$$

The absorbed energy is converted to heat in the medium. This heat input may be used to heat up the medium, or to cause a phase change from liquid to vapor or to cause desorption of analyte from the medium. For an increase in temperature, the following relationship holds:

$$P_a = m c_p \Delta T / \Delta t$$

where m is the mass of the absorbing medium, $C_p$ is the heat capacity of the absorbing medium, $\Delta T$ is the temperature change and $\Delta t$ is the pulse duration. For a phase change, the corresponding relationship is:

$$P_a = m L_t / \Delta t$$

where $L_t$ is the latent heat of transformation.

As an example of the behavior of the system according to the invention, consider a perturbing pulse of one second duration with an input power of 250 mW. Consider a 10 cm long optic fiber with a 200 μm core coated with 2 micron thick cladding layer of silica dioxide containing a small amount of an infrared absorbing dye having an optical density of 1.0 at 830 nm. The molar absorption coefficient $\epsilon$ of laser dye IR-140 made by the Eastman Kodak Company is $1.5 \times 10^5$ L/mole-cm. The absorbed power is 225 mW. The density of silica dioxide is 2 g/cc. The volume of the absorbing material is $1.27 \times 10^{-7}$ cc. If it is assumed that no heat diffuses out of the core of the fiber, the possible equilibrium temperature rise for silica dioxide ($c_p = 10.62$ cal/deg-mole = 0.74 J/g) calculates to be $1.2 \times 10^6$ degrees Centigrade, an obviously unrealistic number. But since the heat actually will diffuse into the entire volume of the fiber, the active volume would be 0.013 cc and the equilibrium temperature rise calculates to be 11.7 degrees Centigrade for the 1 second perturbation pulse, assuming the heat is confined to the 10 cm long fiber section. In actual practice, a much lower temperature rise would be expected due to material transformations.

By measuring the time rate of change of the intensity of the radiant energy emitted before, during or after such perturbing pulses or during all three periods, the concentration of the analyte can be quickly and accurately determined. As indicated schematically in FIG. 1, a controller 24, such as a general purpose computer, directs the operation of sources 16 and 22. In accordance with the invention, a conventional slope detector 26, which may actually be part of controller 24, receives the output of detector 18, determines the time rate of change of the intensity and transmits the rate of change to controller 24. A look-up table is provided in controller 24 which relates particular combinations of time, intensity and slope to particular concentrations of the analyte, based on previously completed calibration data for a given analyte. Controller 24 then correlates the measured times, slopes and intensities to the concentration of the analyte and provides an output to a display 28.

Figure 2:
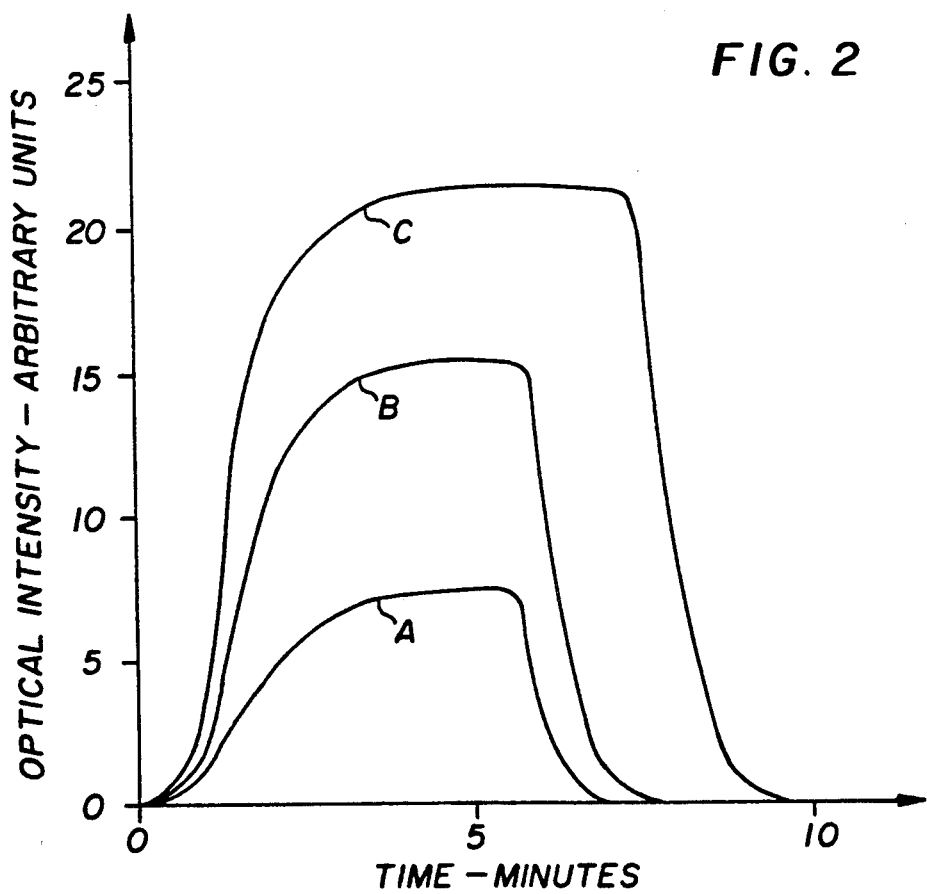
FIG. 2 illustrates graphically the nature of the response of prior art optical sensors to step changes in the concentration of the analyte.

FIG. 2 illustrates graphically how typical prior art optical sensors respond to step changes in the concentration of an analyte in the ambient medium. The presentation of FIG. 2 is based on data reported by Mahmoud R. Shahriari, George H. Sigel and Quan Zhou in an article entitled "Porous Fiber Optic for a High Sensitivity Humidity Sensor", (Rutgers University, Fiber Optic Materials Research Program) *Proceedings of the Optical Fiber Society*, January 1988, pages 373-381; however, the nature of the response shown is typical for known optical sensors of the types discussed in this specification under the heading Background Art. As shown in FIG. 2, step increases A, B and C in the concentration of the analyte of interest produce an increasing intensity of transmitted light until a plateau is reached. Then, when the analyte of interest is removed, the intensity decays back to a base line value. As indicated in FIG. 2, the time to reach a stable value is on the order of minutes for detection of humidity and also is on the order of minutes to decay back to a base line value. Similar long times to reach stable values have been reported for other types of sensors.

Figure 3:
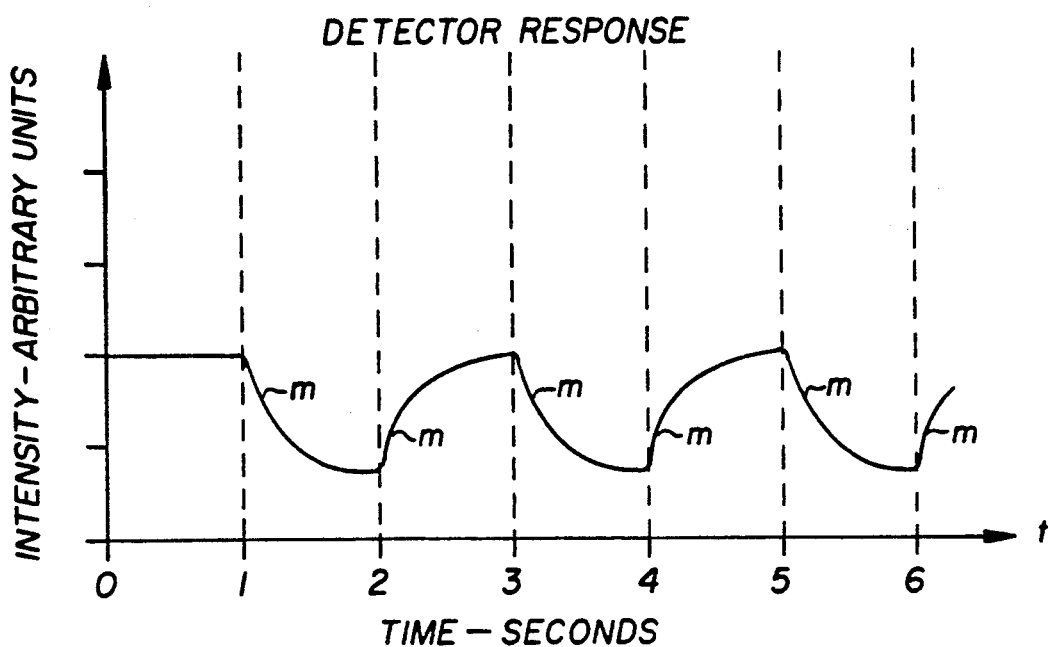
FIGS. 3 and 4 illustrate graphically the nature of the response of an optic fiber system in accordance with the invention.
Figure 4:
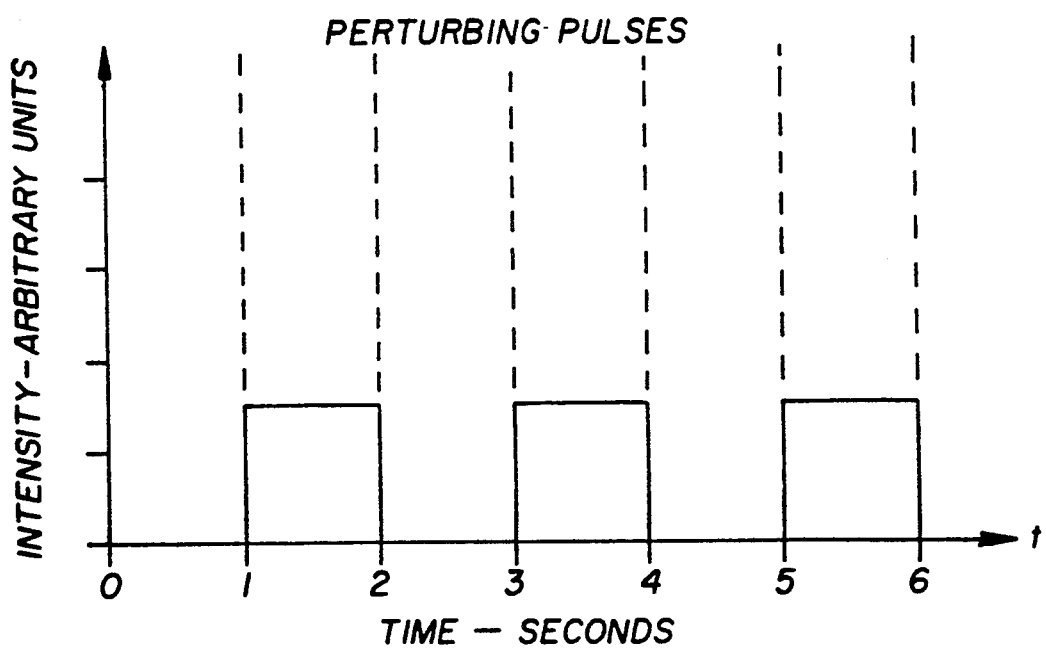

In accordance with the present invention, it has been discovered that for a given level of intensity, the increasing and decreasing rates of change of the intensity with respect to time are proportional to the concentration of the analyte of interest. Thus, using the apparatus of FIG. 1, the concentration of an analyte can be measured rapidly and accurately. FIGS. 3 and 4 illustrate graphically how the intensity of light reaching detector 18 changes for a constant concentration of analyte in response to perturbing pulses from source 22 for reagents whose optical absorption increases in response to the perturbing pulse. Similar responses are achieved if the concentration is increasing or decreasing at the time of measurement. If the sensor quenches absorption or fluorescence in response to changes in the concentration of the analyte, the signals would change in the opposite directions. In either event, for a given concentration of analyte, the time rates of change of the increasing and decreasing intensity have characteristic values at given times and levels of intensity, which can be determined for a given combination of reagent and analyte and stored in controller 24 as previously mentioned. In the example of FIG. 3, the intensity initially is shown to be constant, indicating a constant concentration of analyte and stable conditions, until a perturbing pulse of radiant energy is applied from source 22, which causes the intensity to begin to decline due to the effect of the perturbing pulse on the analyte in coating 14. Actually, the heat of the perturbing pulse drives off at least a portion of the analyte; so that, the level of intensity drops to a certain base line magnitude. To calibrate the apparatus, a family of curves such as shown in FIGS. 3 and 4 is plotted for various concentrations of the analyte. These curves are then fitted to exponential or polynomial expressions which permit a determination of the slope of the curve as a function of time and concentration of the analyte. As will be understood by those skilled in the art, inspection of the family of curves indicates points in time while the intensity is changing due to the perturbing pulse, after each perturbing pulse starts or ends or both, at which the slope of the curve should be measured to provide an accurate measurement of concentration of the analyte. For a first order system, slopes measured at one point in time typically will provide an accurate measurement; whereas, for second and higher order systems, slopes measured at two or more times will be needed to accurately measure the concentration. If the signal to noise ratio is not favorable, the slopes can be measured over many cycles and averaged to provide more accurate readings.

In a medium in which water is converted from liquid to vapor by the perturbing pulse, a pulse having a power of 225 mW for one second can convert about 0.01 g of liquid water to vapor, the latent heat of water being 22.6 J/g. If a 60 μm thick Millipore filter having a 40% open area is provided around the previously described optic fiber sensor, the filter will have a volume of about 0.005 cc and will hold 0.002 g of water. Hence, the perturbing pulse, if absorbed, can dry up all of the water in the filter in about 0.2 seconds. This behavior was observed using a 200/230 μm polymer clad silica fiber, Model PN 15-200B from General Fiber Optics Corporation. The plastic cladding was stripped off and replaced with a gelatin solution containing 0.02 g/cc of $CoCl_2$ and 0.013 g/cc of Kodak laser dye IR-100. A 10 cm long section of fiber was coated by dipping into the gelatin solution and drying at 100 degrees Centigrade. Caliper measurements and microscopy were used to estimate the coating thickness at about 2 μm. A 25 μW, 670 nm LED corresponding to source 16 and a 1 W, 830 nm laser diode corresponding to source 22 were coupled into the sensing medium on the fiber by means of a conventional Amphenol 2×1 coupler. A photodetector was placed at the other end of the fiber. At 25% relative humidity, the sensing fiber had an effective optical density of 1.2 at 670 nm; and at 95% relative humidity, it had an effective optical density of 0.2 at 670 nm. The absorbance at 830 nm was 1.0 independent of relative humidity. The active sensor region was wrapped in a 60 μm thick Millipore filter with 40% open area and dipped into water. An inline filter was placed before the detector to cut off light above 730 nm. When tested, the active sensor region appeared pink in water. When the laser perturbing pulse was turned on for one second at one second intervals, the sensor region turned bluish within about 0.3 seconds. As indicated at "m" in FIG. 3, the time rate of change of the intensity in such a system can be measured while the intensity is changing due to the perturbing pulse, after each perturbing pulse starts or ends or both, the precise times for measurement being determined during calibration as previously described.

In the sensor shown in FIG. 1 and described in the preceding example, the analyte is absorbed by the reagent in coating 14 causing a change in the intensity of the radiant energy transmitted by optic fiber 10. The perturbing pulse drives off some of the analyte to produce changes in intensity of the type shown in FIG. 3. However, the invention also is useful where the reagent fluoresces and the analyte causes a change in such fluorescence. For example, a reagent such as perylene dibutryate can be applied to optic fiber 10 by means of coating in gelatin and will tend to fluoresce when the beam of radiant energy from source 16 is at 450 nm and the intensity of such fluorescence will be a function of the concentration of oxygen in the ambient medium. Then, when a pulse at 350 nm is applied, the analyte will be driven from the reagent to produce changes in the intensity of fluorescence of the general type shown in FIG. 3. Similarly, if a reagent such as polyvinylpyridene is coated onto a reflective surface toward which optic fiber 10 emits radiant energy, the degree of reflectiveness of the surface will be a function of the concentration of halogenated organics in the ambient medium. In this case, if a perturbing pulse at 920 nm is applied, the analyte will be driven from the coated surface of the mirror to produce changes in reflectivity of the same general type. And, if a detection is to be made by measuring Raman scattered radiant energy, a reagent such as a porous sol gel with absorbed dye can be coated onto the fiber; and the intensity of the scattering measured at a given angle will be a function of analyte concentration in the medium when looking at a specific analyte band. Then, if perturbing pulses at the absorption maximum of the dye are applied, the analyte will be driven off to produce changes in the intensity of the scattering of the same general type. Thus, the application of perturbing pulses and slope measurements in accordance with the invention can be applied to a wide range of analytes and sensing reagents.

The invention also can be applied to measure concentrations in fluid mediums of analytes which react directly to radiant energy by fluorescing or by absorbing, scattering or reflecting a portion of the radiant energy. As in the case where a reagent is used, the reaction between the analyte and the radiant energy must be alterable in a controlled manner due to the application of a perturbing pulse of energy. If the presence of the analyte in the medium causes a change in the intensity of the radiant energy transmitted through plenum 12 from optic fiber 10, the analyte affects the tendency of the medium to absorb radiant energy. For example, an analyte such as copper ions in a medium such as water will show high absorption at 820 nm. In such a case, a perturbing pulse drives off some of the analyte in the light path to produce changes in intensity of the type shown in FIG. 3. The invention also is useful where the medium fluoresces and the analyte causes a change in such fluorescence. Various phenolics will tend to fluoresce when the beam of ultraviolet radiant energy is applied from source 16 and the intensity of such fluorescence will be a function of the concentration of phenolics in the ambient medium. Then, when a perturbing pulse is applied, the phenolics will be driven from the light path to produce changes in the intensity of fluorescence of the general type shown in FIG. 3. Similarly, if an analyte is present in front of a reflective surface toward which optic fiber 10 emits radiant energy, the amount of reflected energy at a first absorption band of the analyte will be a function of the concentration of the analyte in the medium. In such a case, if a perturbing pulse is applied at a second absorption band of the analyte, the analyte will be driven from the light path to produce changes in the response. And, if a detection is to be made by measuring scattered radiant energy, the intensity of the scattered radiation, such as fluorescence or Raman scattering, will be a function of the concentration of the analyte in the medium. Then, if perturbing pulses in an absorption band of the analyte are applied, the analyte will be driven from the light path to produce changes in the intensity of the scattering of the same general type. Thus, the application of perturbing pulses and slope measurements in accordance with the invention can be applied to a wide range of analytes and media.

Figure 5:
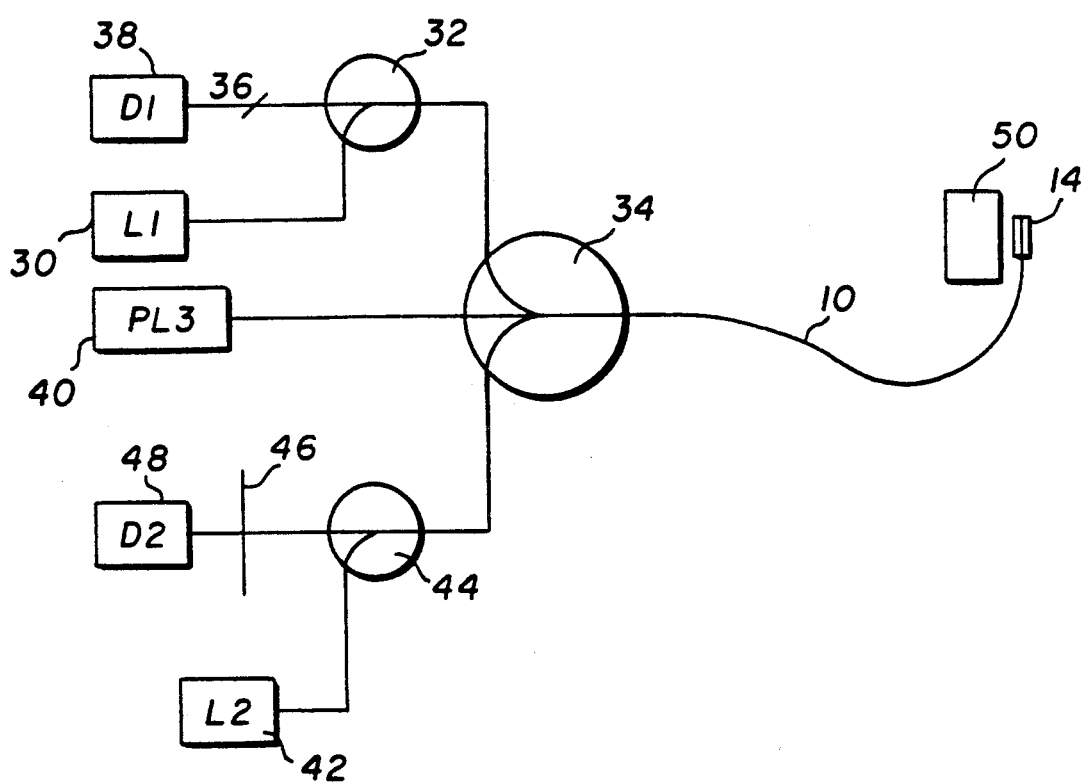
FIG. 5 illustrates schematically another embodiment of the invention in which dual light sources are coupled to a single sensor element.

FIG. 5 illustrates an alternative embodiment of the invention which comprises multiple light sources and a reflective sensor. In this instance, coating 14 is applied to the tip of fiber 10; so that, as the concentration of the analyte changes, the intensity of the light reflected back along the fiber changes. A preferably continuous beam of radiant energy is launched from a source 30 into fiber 10 via couplers 32 and 34 at a first wavelength and power level at which the sensitivity of coating 14 is optimized for changes in the concentration of the analyte in the medium surrounding coating 14. At least a portion of the radiant energy is reflected back along fiber 10 via couplers 34 and 32, through an optional filter 36 to a detector 38. A second, pulsed source of radiant energy 40 periodically launches perturbing pulses of radiant energy into fiber 10 via coupler 34. The perturbing pulses are at a wavelength and power level selected to alter in a controlled manner the effect of the analyte on the reagent in coating 14, thereby changing the effect of the coating on the radiant energy reflected back along fiber 10 to detector 38. At the same time, a preferably continuous beam of radiant energy is launched from a third source 42 into fiber 10 via couplers 44 and 34 at a second wavelength and power level at which the sensitivity of coating 14 is optimized for changes in the concentration of the analyte in the surrounding medium. Alternatively, the radiant energy from source 40 may be selected to cause coating 14 to be sensitive to a different analyte. It is also within the scope of the invention to include in coating 14 two or more reagents which respond differently to a given analyte or to different analytes, thus permitting confirming measurements for one analyte or measurements for different analytes with a single sensor. In either event, the pulses from source 40 alter in a controlled manner the effect of the analyte on the reagent in coating 14, thereby changing the effect of the coating on the radiant energy reflected back along fiber 10 to detector 48. A previously mentioned, the perturbing pulse may be ultraviolet, visible or infrared radiant energy; acoustic energy; energy from an electrical or magnetic field; energy from a microwave generator or energy from a heat source, depending on the reagent and the analyte under consideration. If a perturbing pulse in a from other than radiant energy is to be used, a conventional source 50 for such pulse may be located near coating 14, as indicated schematically in both FIGS. 1 and 5, to permit application of the perturbing pulse.

While my invention has been shown and described with reference to particular embodiments thereof, those skilled in the art will understand that other variations in form and detail may be made without departing from the scope and spirit of my invention.

Having thus described my invention in sufficient detail to enable those skilled in the art to make and use it, I claim as new and desire to secure Letters Patent for:

1. A method for measuring the concentration of an analyte in a medium, comprising the steps of:
   directing a beam of radiant energy along an optical path into said medium at a wavelength selected to cause a response of said analyte;
   periodically directing a perturbing pulse of energy into said medium to alter in a controlled manner the concentration of said analyte along said path and thereby the response of said analyte to said beam of radiant energy;
   detecting the response of said analyte to said beam of radiant energy while the response is changing due to the influence of the perturbing pulse, after the perturbing pulse starts or ends or both;
   determining the time rate of change of said response; and correlating said time rate of change to the concentration of said analyte.

2. A method according to claim 1, wherein said medium is a fluid and said analyte responds to said beam of radiant energy by fluorescing.

3. A method according to claim 1, wherein said medium is a fluid and said analyte responds to said beam of radiant energy by absorbing at least a portion of said radiant energy.

4. A method according to claim 1, wherein said medium is a fluid and said analyte responds to said beam of radiant energy by scattering at least a portion of said radiant energy.

5. A method according to claim 1, wherein said medium is a fluid and said analyte responds to said beam of radiant energy by reflecting at least a portion of said radiant energy.

6. A method according to one of claims 1 to 5, wherein said response is a change in the intensity of radiation leaving said medium.

7. A method according to claim 1, wherein said perturbing pulse comprises acoustic energy.

8. A method according to claim 1, wherein said perturbing pulse comprises energy from an electrical field.

9. A method according to claim 1, wherein said perturbing pulse comprises energy from a magnetic field.

10. A method according to claim 1, wherein said perturbing pulse comprises ultraviolet, visible or infrared radiant energy.

11. A method according to claim 1, wherein said perturbing pulse comprises microwave energy.

12. A method according to claim 1, wherein said perturbing pulse comprises heat energy.

13. A method for measuring the concentration of an analyte in a medium, comprising the steps of:
providing a reagent whose optical properties change in response to the concentrations of said analyte;
exposing said reagent to said analyte in said medium;
directing a beam of radiant energy along an optical path into said reagent at a wavelength selected to affect said beam of radiant energy as a function of the concentration of said analyte;
periodically directing a perturbing pulse of energy into said reagent to alter in a controlled manner both the concentration of said analyte along said path and the optical spectral characteristics of said reagents as a function of the concentration of said analyte;
detecting the effect of said reagent on said beam of radiant energy while the response is changing due to the influence of the perturbing pulse, after the perturbing pulse starts or ends or both;
determining the time rate of change of said effect; and
correlating said time rate of change to the concentration of said analyte.

14. A method according to claim 13, wherein said optical property of said reagent is fluorescence.

15. A method according to claim 13, wherein said optical property of said reagent is absorbance.

16. A method according to claim 13, wherein said optical property of said reagent is its ability to scatter at least a portion of said radiant energy.

17. A method according to claim 13, wherein said optical property of said reagent is its ability to reflect at least a portion of said radiant energy.

18. A method according to one of claims 13 to 17, wherein said effect is a change in the intensity of radiation leaving said medium.

19. A method according to claim 13, wherein said perturbing pulse comprises acoustic energy.

20. A method according to claim 13, wherein said perturbing pulse comprises energy from an electrical field.

21. A method according to claim 13, wherein said perturbing pulse comprises energy from a magnetic field.

22. A method according to claim 13, wherein said perturbing pulse comprises ultraviolet, visible or infrared radiant energy.

23. A method according to claim 13, wherein said perturbing pulse comprises microwave energy.

24. A method according to claim 13, wherein said perturbing pulse comprises heat energy.

25. Apparatus for measuring the concentration of an analyte in a medium, comprising:
means for directing a beam of radiant energy along an optical path into said medium at a first wavelength selected to cause a response of said analyte;
means for periodically directing a perturbing pulse of energy into said medium and for altering in a controlled manner the concentration of said analyte along said path and thereby the response of said analyte to said beam of radiant energy;
means for detecting the time rate of change of the intensity of radiation leaving said medium as the response of said analyte to said beam of radiant energy while the response is changing due to the influence of the perturbing pulse, after the perturbing pulse starts or ends or both; and
means for correlating said time rate of change to the concentration of said analyte.

26. Apparatus according to claim 25, wherein said medium is a fluid and said analyte responds to said beam of radiant energy by fluorescing.

27. Apparatus according to claim 25, wherein said medium is a fluid and said analyte responds to said beam of radiant energy by absorbing at least a portion of said radiant energy.

28. Apparatus according to claim 25, wherein said medium is a fluid and said analyte responds to said beam of radiant energy by scattering at least a portion of said radiant energy.

29. Apparatus according to claim 25, wherein said medium is a fluid and said analyte responds to said beam of radiant energy by reflecting at least a portion of said radiant energy.

30. Apparatus according to claim 25, wherein said perturbing pulse comprises acoustic energy.

31. Apparatus according to claim 25, wherein said perturbing pulse comprises energy from an electrical field.

32. Apparatus according to claim 25, wherein said perturbing pulse comprises energy from a magnetic field.

33. Apparatus according to claim 25, wherein said perturbing pulse comprises ultraviolet, visible or infrared radiant energy.

34. Apparatus according to claim 25, wherein said perturbing pulse comprises microwave energy.

35. Apparatus according to claim 25, wherein said perturbing pulse comprises heat energy.

36. Apparatus according to claim 25, wherein said medium is a waveguide.

37. Apparatus according to claim 25, wherein said means for directing a beam comprises a continuous source of radiant energy and an optic fiber for receiving radiant energy from said continuous source at one end and emitting radiant energy from said continuous source into said medium at the other end.

38. Apparatus according to claim 37, wherein said means for directing a perturbing pulse comprises an intermittent source of radiant energy and means for coupling radiation from said intermittent source into said optic fiber.

39. Apparatus according to claim 37, wherein said means for directing a perturbing pulse comprises an intermittent source of radiant energy and an optic fiber for receiving said pulse at one end and emitting said pulse onto said medium at the other end.

40. Apparatus for measuring the concentration of an analyte in a medium, comprising:
a sensor element including a reagent whose optical properties change in response to the concentration of said analyte;
means for exposing said reagent to said analyte in said medium;
means for directing a beam of radiant energy along an optical path into said reagent at a wavelength selected to affect said beam of radiant energy as a function of the concentration of said analyte;

means for periodically directing a perturbing pulse of energy into said reagent and for altering in a controlled manner both concentration of said analyte along said path and the optical spectral characteristics of said reagent as a function of the concentration of said analyte;

means for detecting the time rate of change of the intensity of radiation leaving said reagent as the effect of said reagent on said beam of radiant energy while said effect is changing due to the influence of the perturbing pulse, after the perturbing pulse starts or ends or both; and means for correlating said time rate of change to the concentration of said analyte.

41. Apparatus according to claim 40, wherein said optical property of said reagent is fluorescence.

42. Apparatus according to claim 40, wherein said optical property of said reagent is absorbance.

43. Apparatus according to claim 40, wherein said optical property of said reagent is its ability to scatter at least a portion of said radiant energy.

44. Apparatus according to claim 40, wherein said optical property of said reagent is its ability to reflect at least a portion of said radiant energy.

45. apparatus according to claim 40, wherein said means for directing a perturbing pulse comprises an intermittent source of radiant energy and an optic fiber for receiving said pulse at one end and emitting said pulse into said sensor.

46. Apparatus according to claim 40, wherein said perturbing pulse comprises acoustic energy.

47. Apparatus according to claim 40, wherein said perturbing pulse comprises energy from an electrical field.

48. Apparatus according to claim 40, wherein said perturbing pulse comprises energy from a magnetic field.

49. Apparatus according to claim 40, wherein said perturbing pulse comprises ultraviolet, visible or infrared radiant energy.

50. Apparatus according to claim 40, wherein said perturbing pulse comprises microwave energy.

51. Apparatus according to claim 40, wherein said perturbing pulse comprises heat energy.

52. Apparatus according to claim 40, wherein said sensor element comprises waveguide having a coating including said reagent.

53. Apparatus according to claim 40, wherein said means for directing a beam comprises a continuous source of radiant energy and an optic fiber for receiving radiant energy from said continuous source at one end and emitting radiant energy from said continuous source into said sensor.

54. Apparatus according to claim 53, wherein said means for directing a perturbing pulse comprises an intermittent source of radiant energy and means for coupling radiation from said intermittent source into said optic fiber.

55. Apparatus according to claim 53, wherein said sensor element comprises a portion of said optic fiber and said reagent is comprised in a reflective coating on the tip of said optic fiber.

56. Apparatus according to claim 53, wherein said sensor element comprises a portion of said optic fiber and said reagent is comprised in a coating surrounding at least a portion of said optic fiber.

* * * * *